(12) United States Patent
Jiang et al.

(10) Patent No.: US 7,265,829 B2
(45) Date of Patent: Sep. 4, 2007

(54) REFLECTIVE OPTIC SYSTEM FOR IMAGING MICROPLATE READERS

(75) Inventors: Wu Jiang, Sunnyvale, CA (US); Todd E. French, Sunnyvale, CA (US); David P. Stumbo, Belmont, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 264 days.

(21) Appl. No.: 10/738,438

(22) Filed: Dec. 17, 2003

(65) Prior Publication Data
US 2004/0233545 A1 Nov. 25, 2004

Related U.S. Application Data
(60) Provisional application No. 60/434,291, filed on Dec. 17, 2002.

(51) Int. Cl.
*G01J 3/28* (2006.01)
(52) U.S. Cl. ...................................... 356/328
(58) Field of Classification Search ........ 356/317–318, 356/417; 359/648–651, 724–730, 735, 754, 359/850, 856, 807, 858, 859
See application file for complete search history.

(56) References Cited

U.S. PATENT DOCUMENTS

| | | | | |
|---|---|---|---|---|
| 2,585,009 A | * | 2/1952 | Henroteau | 348/783 |
| 3,926,505 A | * | 12/1975 | Rayces | 359/731 |
| 4,205,902 A | * | 6/1980 | Shafer | 359/366 |
| 4,501,475 A | * | 2/1985 | Fujita et al. | 359/683 |
| 4,554,448 A | * | 11/1985 | Sillitto | 250/216 |
| 4,861,148 A | * | 8/1989 | Sato et al. | 359/366 |
| 5,136,413 A | * | 8/1992 | MacDonald et al. | 359/213 |
| 5,355,215 A | | 10/1994 | Schroeder et al. | |

(Continued)

FOREIGN PATENT DOCUMENTS

DE 19828547 A1 * 1/2000

OTHER PUBLICATIONS

Shealy, et al., "Design and analysis of aspherical multilayer imaging x-ray microscopic", *Optical Engineering*, vol. 30, pp. 1094-1909 (1991).

(Continued)

*Primary Examiner*—Tu T. Nguyen
(74) *Attorney, Agent, or Firm*—Morgan, Lewis & Bockius LLP; David J. Brezner; Victor E. Johnson

(57) ABSTRACT

A reflective light imaging system for use in high-throughput screening of samples disposed in multiple-well plates. The system can include a set of mirrors and lenses. The first mirror has a central aperture through which light from the object passes. The first mirror has a concave reflective surface that faces the image plane. The next element is a second mirror with a convex reflective surface. The system can include an aberration corrective system positioned between the second mirror and the image plane, and an optical sensor near the image plane. Light from an object passes through the central aperture of the first mirror and is reflected off the convex surface of the second mirror. The light then strikes the reflective surface of the first mirror. The light from the first mirror is then collected by the aberration correction system and transmitted toward the image plane.

31 Claims, 2 Drawing Sheets

U.S. PATENT DOCUMENTS

| | | |
|---|---|---|
| 5,757,552 A | 5/1998 | Murayama et al. |
| 6,128,139 A | 10/2000 | Fukutake |
| 6,198,577 B1 * | 3/2001 | Kedar et al. ................ 359/663 |
| 6,309,601 B1 | 10/2001 | Juncosa et al. |
| 6,316,774 B1 | 11/2001 | Giebeler et al. |
| 6,372,485 B1 | 4/2002 | Clark et al. |
| 6,392,814 B1 | 5/2002 | Ono |
| 6,469,311 B1 | 10/2002 | Modlin et al. |
| 6,483,588 B1 * | 11/2002 | Graefe et al. ............... 356/436 |
| 6,636,361 B2 * | 10/2003 | Wada ......................... 359/680 |

OTHER PUBLICATIONS

Product Brochure, Reflecting Microscope Objectives (Sep. 2001).

* cited by examiner

REFLECTIVE OPTIC SYSTEM FOR IMAGING MICROPLATE READERS

This application claims benefit to the filing date of Provisional Patent Application Ser. No. 60/434,291, filed on Dec. 17, 2002, the contents of which are incorporated herein by reference.

BACKGROUND

1. Field of the Invention

This invention relates generally to fluorescence and luminescence analytical techniques, and, more specifically, to an optical system that permits high-throughput, simultaneous measuring of the fluorescence or luminescence of a plurality of samples disposed in a multi-well plate.

2. Background of the Invention

Fluorescence and luminescence measurements are employed in a variety of analyses, and in such-techniques, illumination of a first wavelength absorbed by a sample induces the sample to emit light of a second wavelength. The wavelength and/or intensity of the secondary emission may be correlated with composition, concentration, physical environment and similar parameters. In one particular class of fluorescence analyses, cells of various tissue types are grown in culture and incubated in a growth medium with a fluorescent dye. The cells will absorb the dye at particular rates, and these rates may be correlated with various physiological functions of the cells, such as $K^+$ channel activity. A cell that has absorbed dye will typically fluoresce at an enhanced intensity as compared to the growth medium that incorporates that dye. In another class of fluorescence analyses, cells are incubated with fluorescent dye that changes its fluorescence depending on the concentration of an analyte within the cell. Typical analytes are $Ca^{++}$, $Na^+$, or $H^+$. These concentration changes assayed are commonly transient. For fast sample processing this class of assays requires simultaneous initiation of reaction (conventionally by injecting a final chemical component) and simultaneous measurement of each sample Fluorescent analyses of these types are of significant importance in the pharmaceutical industry since they may be employed to screen a variety of tissue types for interaction with chemical species of pharmaceutical interest In an analysis of these types, cells are cultured in a multiple well plate. These plates have typically included 96 or 384 wells, each well comprising a cylinder of approximately 5 millimeters in diameter or smaller. Each well is closed at one end by an optically transparent bottom, surface and open at the other. The cells are cultured in a layer on the bottom surface of the wells with a supernatant layer of growth medium. Chemical species being assayed are placed into the supernatant liquid together with a fluorescent dye, and the effect of the chemical species on cell metabolism is assayed by measuring the fluorescence of the cell layers.

In order to measure the fluorescence of the cells, the cell layers are illuminated with light of a first wavelength, and light emission at a second wavelength is monitored by an optical detector. Fluorescence can be measured with a microscopic optical system, which limits background fluorescence due to the limited depth of field. However, the severely limited field of view of such systems reduces overall assay throughput. Effective high-throughput cell-based assays require simultaneous reading of entire well plates, which in turn requires efficient illuminating and detecting optics that allow wide-field imaging.

SUMMARY OF THE INVENTION

In a first aspect, a reflective light imaging system is disclosed. The system can measure light from an object, such as a multiple-well microtiter plate. The system can include a first mirror with a central aperture and a concave reflective surface, the concave reflective surface facing an image plane opposite the object. The system can also include a second mirror comprising a convex reflective surface facing the object side, wherein light from an object passes through the central aperture of the first mirror and is reflected by the convex reflective surface toward the concave reflective surface of the first mirror.

The system can also include an aberration correction system that collects the light reflected from the first mirror and transmits it toward the image plane. The aberration correction system can correct for off-axis optical aberrations that may be present if the object is large (resulting in a wide field of view).

In a second aspect, the system may be used for simultaneously measuring luminescence from each of a plurality of samples disposed in a multiple-well plate, and can optionally include, in addition to the elements described above, a light source that illuminates the object. The illumination can be of a first wavelength that excites the fluorescent emission of light of a second wavelength from the plurality of samples. The system can also measure luminescence from the samples in the absence of a separate illumination source.

The system may also include an optical sensor that is responsive to the second wavelength of light from the plurality of samples, the sensor being positioned to receive light from the light imaging system.

BRIEF DESCRIPTION OF THE SEVERAL VIEWS OF THE DRAWINGS

Exemplary embodiments of the present system are described herein with reference to the drawings, in which.

DETAILED DESCRIPTION OF AN EXEMPLARY EMBODIMENT

Figure 1:
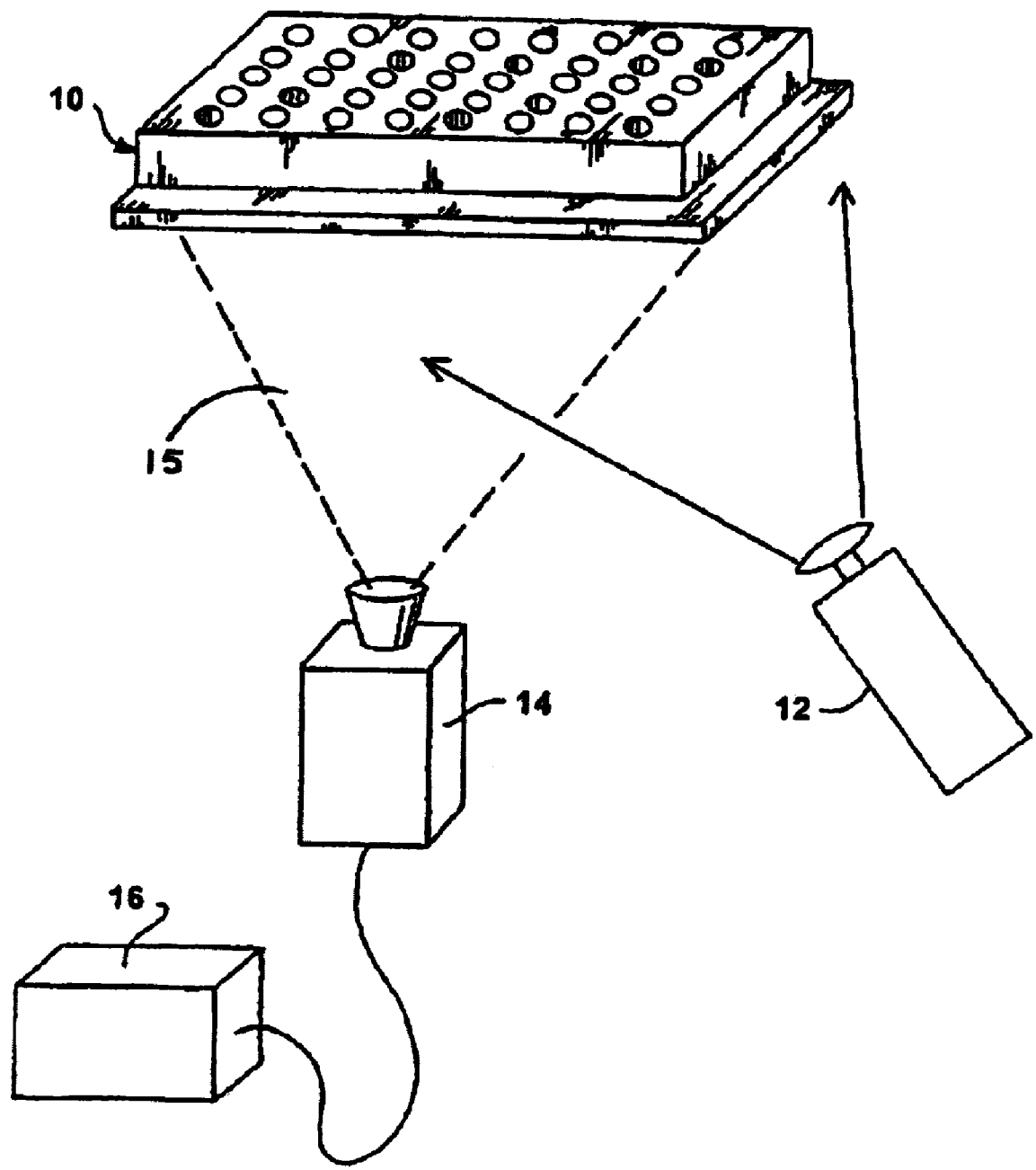
FIG. 1 is a schematic of a measurement apparatus in which an exemplary embodiment of the present system can be implemented.

Typically, optics to image multi-well plates include very large refractive systems, with many lens elements. Plates having up to 1,536 wells, however, present a problem for conventional optics because each well is necessarily smaller than wells of a 384 well plate used in conventional systems, and accordingly samples in the wells produce less total light. In addition, higher optical resolution is required, and must be available over a relatively wide field. A wide field of View is desirable for high throughput, as it permits a 1,536 well plate to be imaged simultaneously with high efficiency.

Illuminating multi-well plates with lasers can enable simultaneous imaging due to the intensity of lasers. Laser illumination, however, can be troublesome because the high-powered lasers used may require three-phase electrical power and their own water-cooling systems. Further, laser illumination is not color versatile—that is, it lacks the ability to excite samples at a wide variety of wavelengths. Lasers do provide very bright illumination, however, which mitigates transmissive losses that are inherent with large, multi-lens refractive optical systems.

Thus, there is a need for optic systems that can read large, 1,536-well plates using conventional non-laser (i.e., less intense) light sources, and that are efficient enough to read fluorescent samples. Conventional optical systems that are possibly capable of meeting this need are bulky and extremely expensive, and may not be sensitive enough for use with non-laser illumination. The innovative reflective optical systems of this invention can provide image quality comparable to or better than that of a refractive system, but with greater light transmitting efficiency, less bulk, and possibly less expense. The light transmitting efficiency of such a reflective optical system can enable illumination of large multi-well plates by color-versatile sources, and may enable simultaneous reading of luminescent samples.

The invention embodiments described here are suitable for assays such as kinetic and cellular assays that involve reading the samples (i.e., taking a measurement) before (prereading) and after (reading) initiation of the kinetic or cellular assay, since the pre-initiation measurement may act as a reference or calibration for the post-initiation measurement. Initiation of a kinetic assay may be accomplished by addition of a key assay component (e.g., via fluid transfer), electrical stimulation (e.g., via field-stimulating cells for electrically responsive assays or electrochemiluminescent assays), and/or photoactivation of key assay components and other similar means. Suitable field-stimulating cells are described in U.S. patent application Ser. No. 09/934,348, filed. Aug. 20, 2001, the specification of which is hereby incorporated by reference in its entirety for all purposes. The present system can be used in conjunction with an apparatus and method that enables photoactivation by a tunable light source that can be configured to quickly send one burst of energy (e.g., a pulse) to initiate the assay, followed by the monitoring wavelength used to induce luminescence.

Based on calculations, the optical system described herein, when used in conjunction with a large 18 mm×12 mm charge-coupled device (CCD), could achieve a 2× throughput improvement and a 1.4× signal-to-noise improvement when used with a 1,536-well plate, compared to existing 384-well detecting systems. The optical system may be used in conjunction with the measurement system generally described in U.S. Pat. Nos. 5,355,215, 6,198,577, 6,271,972, and 6,476,976 (fluorescence, scintillation, chemiluminescence detection systems), the specifications of which are hereby incorporated by reference in their entirety.

Referring now to the drawings, FIG. 1 is a schematic view of a measurement apparatus in which the present optical system may be used to measure, in parallel, the fluorescence or luminescence of a plurality of samples disposed in a multi-well plate 10. If fluorometric measurements are to be made, a light source 12 can be used to illuminate, through the transparent plate, samples in the bottoms of the wells.

As shown, light source 12, which can comprise a ring or other suitable geometry, can be offset from the angle at which an optical system 14 views the sample. Optical system 14 can include optical elements as well as one or more charge-coupled devices. Optical system 14 has a field of view 15 that is wide enough to image the entire bottom surface of the well plate 10. As described more fully in U.S. Pat. No. 5,355,215, an offset between the light source and the detector can significantly reduce interference from background luminescence of supernatant liquid above the target sample. To further reduce background fluorescence, a mask (not shown) can also be used. In conjunction with a light source, an excitation filter (not shown) can be used to more sharply define the bandwidth of light from light source 12 that reaches the plate 10. The system described herein is suitable for imaging any light, including UV, visible and IR light.

Associated with the optical system 14 is a processor system 16 that may include a processor, a memory, and an operating system stored in the memory to execute the various functions required of the system. The processor system 16 may be programmed to analyze the signal from optical system 14 to identify the light emitted from each well. The processor system 16 can identify the edges of the regions of interest to be assayed to define sensed regions, the sensed regions being much larger than the area typically sensed in a microscope-based system. This edge detection technique, which can reject light below a given threshold, can eliminate or greatly reduce the need for precise alignment of the plate with the detection system.

The measurement system generally includes at least one light source for delivering light to an object that may comprise a plurality of samples in a multi-well plate, at least one detector for receiving light transmitted from the object, and an optical relay structure for relaying light between the light source, the object, and the detector. The measurement system may limit detection to a sensed volume that is smaller than a discrete sample of the object that is to be measured.

Components of the optical system 14 are chosen to optimize sensitivity and dynamic range for each assay mode supported by the measurement apparatus; thus, optical components with low intrinsic luminescence are chosen. In addition, some components are shared by different assay modes (e.g., luminescence v. fluorescence), whereas other components are unique to a particular mode. For example, photoluminescence intensity and steady-state photoluminescence polarization modes share a light source; time-resolved luminescence modes use their own light sources; and chemiluminescence modes do not use a light source. Similarly, photoluminescence and chemiluminescence modes use different detectors.

The assay modes that may be measured using the exemplary optical system all involve detection of luminescence, which is the emission of light from excited electron states of atoms or molecules. Luminescence generally refers to all kinds of light emission, except incandescence and may include photoluminescence, chemiluminescence, electrochemiluminescence, and scintillation, among others. In photoluminescence, including fluorescence and phosphorescence, the excited electron state is created by the absorption of electromagnetic radiation. In chemiluminescence, which includes bioluminescence, the excited electron state is created by a transfer of chemical energy. In electrochemiluminescence, the excited electron state is created by an electrochemical process. In scintillation, light is generated by the absorption of ionizing particles or photons.

Figure 2:
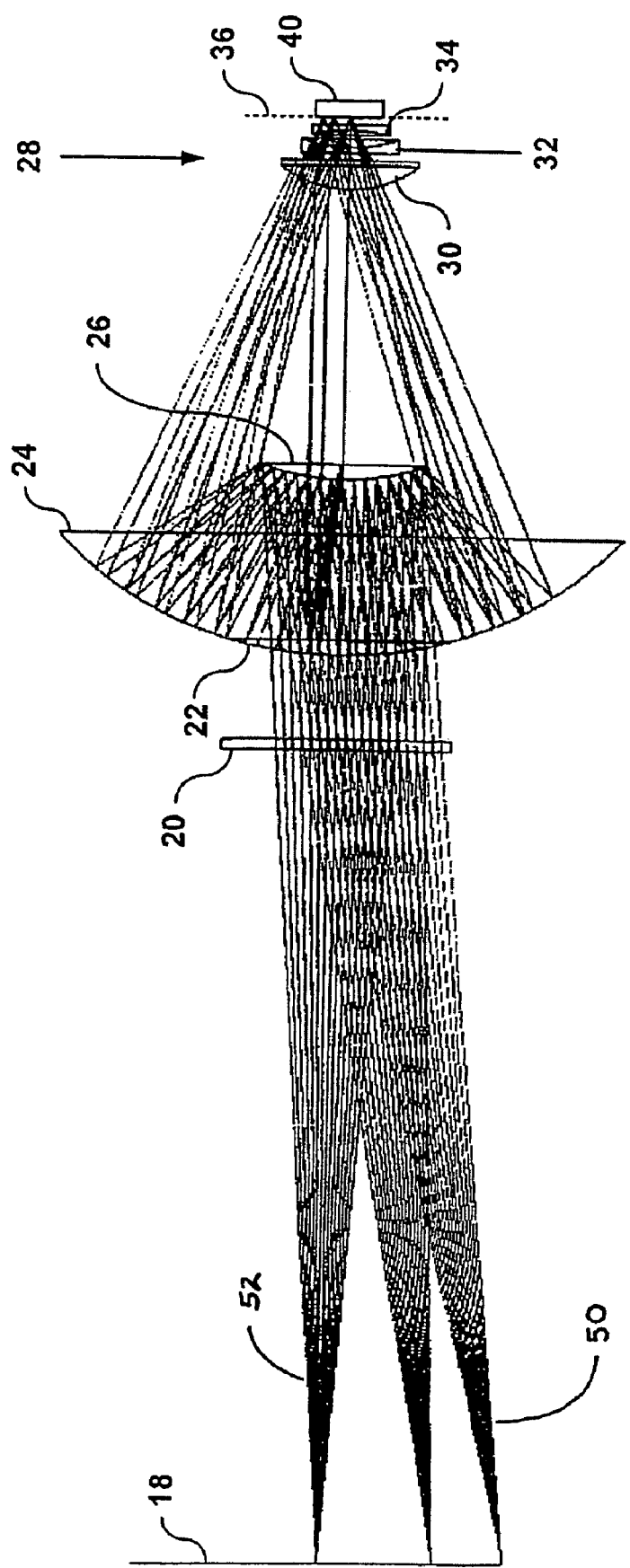
FIG. 2 is a ray diagram of an exemplary embodiment of the present system.

FIG. 2 is a ray diagram of a finite-conjugate reflective light imaging system that may be included in optical system 14. The system shown in FIG. 2 is relatively simple and can be made with standard glass and reflective elements. It also provides high image quality, and it is transmissively efficient, since it has only eight surfaces. During operation, light emitted or reflected from an object 18 (e.g., samples in a multi-well plate) can pass through optical filter 20, which is optional. Filter 20 limits the wavelengths of light that can enter the system, and can thus improve optical performance. Specifically, filter 20 can block light from the excitation source, and light having wavelengths other than those from the samples being measured or monitored.

Light from object 18 next passes through a central aperture 22 in a first mirror 24. The light then strikes, and is reflected from, the convex surface of the second mirror 26 toward the concave reflective surface of the first mirror. Note that only the outer annulus of the second mirror 26 is reflecting useful light. Light that could be reflected by the center portion of the second mirror may be directed back through the central aperture of the first mirror. Hence, the central portion of the second mirror corresponding to the area in which light would be redirected back through the central aperture of the first mirror does not need to be reflective at all. The central portion thus may be treated to be absorptive to remove unwanted light from the optical system, or the central portion may be removed from the second mirror 26 altogether.

The useful light that is reflected by the second mirror is reflected from the concave surface of the first mirror toward an aberration correction system 28 comprising three refractive lenses, lenses 30, 32, and 34, where lens 30 is the closest to the object and lens 34 is the closest to the image plane 36, which is the location of CCD 40.

Additional mirrors (commonly called folding mirrors) can be included in the system to adjust the physical layout without affecting the optical performance. For example, a flat mirror can be placed at 45° between the object and the first mirror to bend the light path 90°, allowing the remaining portion of the light gathering system to be oriented horizontally, rather than under the microplate. This would be advantageous in case of fluid spills from the microplate or nearby fluid handling systems. In principle, folding mirrors may be located anywhere along the optical path. Folding and imaging functions can be combined with curved mirrors that direct the light along a different optic axis after reflection while converging or diverging the same light.

The object 18 may be a relatively large 1,536-well plate that measures 108 mm×72 mm. Measuring such a large object at close proximity with a single optical system can result in significant off-axis optical aberrations, especially when employing spherical optics. Of course, other lens systems, such as refractive systems, could be used to overcome this problem, but such systems present different problems that must be overcome. For example, large refractive systems with many lenses may have lower light transmitting efficiency due to reflective and absorptive losses, so they may not be suitable for use with low light output, high-throughput measurements, as the present reflective system is.

FIG. 2 illustrates the off-axis rays 50 as well as the centered rays 52, both at the object side and as they arrive at the image plane. The aberration correction system 28 compensates for the optical aberrations that could otherwise prevent the system from making useful measurements without scanning (moving the object or optical system); the system permits consistent focusing over a large area. One advantage of the aberration correction system is to make the production and alignment of the first and second mirrors simpler. Both, relatively large, mirrors can be spherical and remaining aberrations due to the wide field imaged by the spherical surfaces are corrected with the, relatively small, correction part of the optical system. Using the correction system also allows the use of a single set of optical elements, rather than multiple refractive parallel lens systems that transmit light to multiple CCDs, which can cause further problems, such as large size, high cost, and the coordination of images from the multiple CCDs. The present optical system, however, could nevertheless be employed in a parallel configuration without all the disadvantages of a purely refractive system, and such a system may have advantages. For example, a multi-lens parallel system could have a wider field of view than a single, non-parallel arrangement, and could require less correction of off-axis aberration.

The particular aberration correction system shown is only one possible system; a system with more or fewer elements is possible, because the only requirement of the correction system is that it corrects for the off-axis aberrations that result from the wide field of view of the system. One or more elements of the correction system can have optical power. The finite-conjugate reflective system shown can image an object over a field of view of at least about 1 degree, preferably above 5 degrees, making the overall system suitable for measuring large 1,536-well plates without scanning. The final corrective element, lens 34, can have a substantially planar surface facing the image plane, which allows for easier adjustment of close coupling to the CCD 40, although such an arrangement is not necessarily critical to all embodiments of the system. Lens 34 can form the optical window of an optical sensor of the system, such as CCD 40.

The object-side Numerical Aperture of the system may be between about 0.01 and about 0.2 preferably, the system NA will have a range of between about 0.01 to about 0.1. The overall magnification range of the system may be from about less than unity or less than 2 with a preferred range of about 0.05 to about 0.5. If the system is used to measure fluorescent emission of light, light source 12 can be designed to provide illumination of a first wavelength that excites the fluorescent emission of light of a second wavelength from the samples in the multi-well plate. Systems of excitation that stimulate emission of light of a second wavelength are described in U.S. Pat. No. 5,355,215 and published U.S. Provisional Patent Application 20020109100A1, herein fully incorporated by reference. Charge-coupled device 40 will be responsive to at least light of the second wavelength. The optical system 14 can also be used for measurements made without an excitation light source, as described above.

Some telescopes, microscopes, imaging microplate readers, and projection systems share some features with the present system, but there are significant differences, illustrated in the following Table A.

TABLE A

| FEATURE | NOT APPLICABLE TO AT LEAST: |
|---|---|
| Small, convex primary mirror | Microscopes, Telescopes |
| Concave secondary mirror faces away from object | Microscopes, Telescopes |
| Object is larger than image, magnification less than unity | Microscopes |
| Finite conjugate system | Telescopes |
| Large field of view; greater than about 6° | Microscopes, Telescopes, Projection systems |
| Light is collected by a detector at the image plane, without intermediate image planes | Projection systems |

TABLE A-continued

| FEATURE | NOT APPLICABLE TO AT LEAST: |
|---|---|
| Measures luminescence from microplates | Microscopes, Telescopes, Projection systems |
| Employs reflective elements with optical power, including both reflective and refractive elements | Imaging microplate readers |
| Final element (with optical power) forms the optical window/seal of the camera | Imaging microplate readers |

Reproduced below is Table B which represents an embodiment of a design for a conjugate reflective light imaging system of this invention. The Table reports traditional surface data that is understandable by one of ordinary skill in the art of optics. The first surface listed in Table B is the object and the last surface is the image. Surfaces are listed in the order that light travels. Positive numbers are distances toward the image or a center of curvature on the image sides. Negative numbers represent distances toward the object or a center of curvature on the object side. For example, the second mirror (surface 3) is closer to the image than the first (surface 5) and thus there is a negative distance (see, for example FIG. 2 of the application). The first mirror (surface 5) has a central aperture of from about 80 to 100 mm diameter to allow light to pass through the central aperture and strike the second mirror (surface 3).

TABLE B

| Surface # | Radius of Curvature, mm | Thickness, mm | Material | Diameter, mm |
|---|---|---|---|---|
| 0 | Infinite | 220.0 | Air | 130 |
| 1 | Infinite | 5.1 | BK7 | 100 |
| 2 | Infinite | 146.6 | Air | 100 |
| 3 | 91.197 | −116.6 | Aluminum | 64 |
| 5 | 193.740 | 220.0 | Aluminum | 270 |
| 7 | 73.609 | 7.4 | BK7 | 58 |
| 8 | Infinite | 7.9 | Air | 58 |
| 9 | Infinite | 8.0 | F2 | 40 |
| 10 | 131.676 | 4.8 | Air | 32 |
| 11 | −51.900 | 2.0 | BK7 | 30 |
| 12 | Infinite | 3.0 | Air | 30 |
| 14 | Infinite | 0.0 | — | 20 |

Exemplary embodiments of the present system have been illustrated and described. It will be understood, however, that changes and modifications may be made to the system without deviating from the spirit and scope of the system, as defined by the following claims.

What is claimed is:

1. A finite conjugate reflective light imaging system comprising, in order from an object side toward an image plane:
    a first mirror comprising a central aperture and a concave reflective surface, the concave reflective surface facing the image plane;
    a second mirror comprising a convex reflective surface facing the object side, wherein light from an object passes through the central aperture and is reflected by the convex reflective surface toward the concave reflective surface of the first mirror; and
    an aberration correction system that collects the light reflected from the first mirror and transmits it toward the image plane;
    wherein the light is due to photoluminescence emission from the object.

2. The system of claim 1, wherein the positional relationship between the object and the first mirror creates a large angular field of view, greater than about ten degrees.

3. The system of claim 2, wherein the aberration correction system substantially corrects off-axis optical aberrations that result from the large angular field of view.

4. The system of claim 1, wherein the aberration correction system comprises a refractive lens group.

5. The system of claim 4, wherein the refractive lens group comprises at least three lenses.

6. The system of claim 4, wherein a refractive lens that is the closest to the image plane has a substantially planar surface that faces the image plane.

7. The system of claim 5, further comprising an optical sensor responsive to light from the object.

8. The system of claim 7, wherein the optical sensor comprises a charge-coupled device.

9. The system of claim 1, wherein the object comprises a plurality of samples disposed in a multiple-well plate.

10. The system of claim 6, wherein the object comprises a plurality of samples disposed in a multiple-well plate.

11. The system of claim 1, wherein the object side Numerical Aperture is between about 0.01 and about 0.1.

12. The system of claim 1, wherein the magnification of the system is less than about 2.

13. A finite conjugate reflective light imaging system comprising, in order from an object side toward an image plane:
    a first mirror comprising a central aperture and a concave reflective surface, the concave reflective surface facing the image plane, wherein the positional relationship between an object and the fist mirror creates a large angular field of view, greater than about 10 degrees;
    a second mirror comprising a convex reflective surface facing the object side, wherein light from an object passes through the central aperture and is reflected by the convex reflective surface toward the concave reflective surface of the first mirror;
    an aberration correction system comprising a refractive lens group that collects the light reflected from the first mirror and transmits it toward the image plane, wherein the aberration correction system substantially corrects off-axis optical aberrations that result from the large angular field of view;
    wherein the object side Numerical Aperture is between about 0.01 and about 0.2;
    and wherein the magnification of the system is less than about 2; and
    an optical sensor responsive to light from the object.

14. The system of claim 13, wherein the aberration correction system comprises a refractive lens group.

15. The system of claim 13, wherein the light is due to luminescence emission from the object.

16. The system of claim 13, wherein the refractive lens group comprises at least three lenses.

17. The system of claim 13, wherein the optical sensor comprises a charge-coupled device.

18. The system of claim 13, wherein the object comprises a plurality of samples disposed in a multiple-well plate.

19. A system for simultaneously measuring fluorescent emission from each of a plurality of samples disposed in a multiple-well plate, the system comprising:
   a light source that provides illumination of a first wavelength that excites the fluorescent emission of light of a second wavelength from the plurality of samples;
   at finite conjugate reflective light imaging system comprising, in order from an object side toward an image plane;
      a first mirror comprising a central aperture and a concave reflective surface, the concave reflective surface facing the image plane;
      a second mirror comprising a convex reflective surface facing the object side, wherein light from an object passes through the central aperture and is reflected by the convex reflective surface toward the concave reflective surface of the first mirror; and
      an aberration correction system that collects the light reflected from the first mirror and transmits it toward the image plane; and
   an optical sensor that is responsive to the second wavelength of light from the plurality of samples and positioned to receive light from the light imaging system.

20. The system of claim 19, wherein the aberration correction system comprise a refractive lens group.

21. The system of claim 20, wherein the refractive lens group comprises at least three lenses.

22. The system of claim 19, wherein the object side Numerical Aperture is between about 0.01 and about 0.2.

23. The system of claim 19, wherein the magnification of the system is less than about 2.

24. The system of claim 19, wherein the optical sensor comprises a charge-coupled device.

25. A system for simultaneously measuring fluorescent emission from each of a plurality of samples disposed in a multiple-well plate, the system comprising:
   a light source that provides illumination of a first wavelength that excites the fluorescent emission of light of a second wavelength from the plurality of samples;
   a finite conjugate reflective light imaging system comprising, in order from an object side toward an image plane;
      a first mirror comprising a central aperture and a concave reflective surface, the concave reflective surface facing the image plane;
      a second mirror comprising a convex reflective surface facing the object side, wherein light from an object passes through the central aperture and is reflected by the convex reflective surface toward the concave reflective surface of the first mirror; and
      an aberration correction system that collects the light reflected from the first mirror and transmits it toward the image plane, wherein the aberration correction system comprises a refractive lens group;
      wherein the object side Numerical Aperture is between about 0.01 and about 0.2;
      wherein the multiple-well plate is positioned on the object side of the imaging system;
      and wherein the magnification of the system is less than about 2; and
   a charge coupled device responsive to the second wavelength of light and positioned to receive light from the imaging system.

26. A system for simultaneously measuring or monitoring luminescence from a plurality of samples disposed in a multiple-well plate, the system comprising:
   a first reflective surface with optical power that directs light from the plurality of samples toward an image plane; and
   an optical sensor proximate the image plane, the optical sensor being responsive to the luminescence from the plurality of samples and being positioned to receive light from the first reflective surface;
   wherein the first reflective surface faces the image plane and includes a central aperture.

27. The system of claim 26, wherein the luminescence comprises fluorescence.

28. The system of claim 26, further comprising a second reflective surface with optical power, wherein luminescence from the plurality of samples passes through the central aperture and is reflected by the second reflective surface toward the first reflective surface.

29. The system of claim 28, further comprising an aberration correction system that collects the light reflected from the first reflective surface and transmits it toward the image plane.

30. The system of claim 29, wherein the aberration correction system comprises at least one refractive element with optical power, the refractive element forming an optical window of the optical sensor.

31. A system for simultaneously measuring or monitoring fluorescence from a plurality of samples disposed in a multiple-well plate, the system comprising:
   a first reflective surface with optical power that directs light from the plurality of samples toward an image plane, the first reflective surface facing the image plane and including a central aperture;
   a second reflective surface with optical power, wherein luminescence from the plurality of samples passes through the central aperture and is reflected by the second reflective surface toward the first reflective surface;
   an optical sensor proximate the image plane, the optical sensor being responsive to the luminescence from the plurality of samples and being positioned to receive light from the first reflective surface; and
   an aberration correction system that collects the light reflected from the first reflective surface and transmits it toward the image plane, the aberration correction system including at least one refractive element with optical power, the refractive element forming an optical window of the optical sensor.

* * * * *